United States Patent
Hahn et al.

(10) Patent No.: US 11,198,010 B2
(45) Date of Patent: Dec. 14, 2021

(54) PACING-BASED HYPERTENSION THERAPY SAFETY

(71) Applicant: Cardiac Pacemakers, Inc., St. Paul, MN (US)

(72) Inventors: Stephen J. Hahn, Shoreview, MN (US); Pramodsingh Hirasingh Thakur, Woodbury, MN (US); Qi An, Blaine, MN (US); Viktoria A. Averina, Shoreview, MN (US); Krzysztof Z. Siejko, Maple Grove, MN (US); Ramesh Wariar, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 145 days.

(21) Appl. No.: 16/366,823

(22) Filed: Mar. 27, 2019

(65) Prior Publication Data
US 2019/0299009 A1 Oct. 3, 2019

Related U.S. Application Data

(60) Provisional application No. 62/685,454, filed on Jun. 15, 2018, provisional application No. 62/650,260, filed on Mar. 29, 2018.

(51) Int. Cl.
*A61N 1/36* (2006.01)
*A61N 1/365* (2006.01)
(Continued)

(52) U.S. Cl.
CPC .......... *A61N 1/36585* (2013.01); *A61B 5/283* (2021.01); *A61B 5/364* (2021.01);
(Continued)

(58) Field of Classification Search
USPC .......................................................... 607/9
See application file for complete search history.

(56) References Cited

U.S. PATENT DOCUMENTS

| 8,165,674 | B2 | 4/2012 | Levin et al. |
| 8,340,763 | B2 | 12/2012 | Levin et al. |

(Continued)

FOREIGN PATENT DOCUMENTS

| WO | WO-2019191258 A1 | 10/2019 |
| WO | WO-2019191274 A1 | 10/2019 |

OTHER PUBLICATIONS

Dilaveris, Polychronis, et al., "Upgrade to biventricular pacing in patients with pacing-induced heart failure: can resynchronization do the trick?", Europace (2006) 8, 352-357, doi: 10.1093/europace/eul015.
(Continued)

*Primary Examiner* — Nicole F Lavert
(74) *Attorney, Agent, or Firm* — Schwegman Lundberg & Woessner, P.A.

(57) ABSTRACT

This document discusses, among other things, systems and methods to generate a first pacing waveform during a first pacing period and a second pacing waveform during a second pacing period, and alternate the first and second pacing periods to provide pacing-based hypertension therapy to a heart of a patient to reduce patient blood pressure, wherein the first pacing waveform has a first atrioventricular (AV) delay and the second pacing waveform has a second AV delay longer than the first AV delay. Physiologic information can be received from the patient, and one of the first or second pacing period for delivery to the patient can be determined using the received physiologic information.

20 Claims, 8 Drawing Sheets

(51) Int. Cl.
  *A61B 7/00*    (2006.01)
  *A61N 1/368*   (2006.01)
  *A61B 5/283*   (2021.01)
  *A61B 5/364*   (2021.01)
  *A61N 1/362*   (2006.01)
  *A61N 1/372*   (2006.01)

(52) U.S. Cl.
  CPC ............... *A61B 7/00* (2013.01); *A61N 1/365* (2013.01); *A61N 1/3682* (2013.01); *A61N 1/36117* (2013.01); *A61N 1/36564* (2013.01); *A61N 1/3625* (2013.01); *A61N 1/3627* (2013.01); *A61N 1/36507* (2013.01); *A61N 1/36521* (2013.01); *A61N 1/36535* (2013.01); *A61N 1/36542* (2013.01); *A61N 1/36578* (2013.01); *A61N 1/37235* (2013.01)

(56) References Cited

U.S. PATENT DOCUMENTS

| | | | |
|---|---|---|---|
| 8,428,729 | B2 | 4/2013 | Schwartz et al. |
| 8,515,536 | B2 | 8/2013 | Levin et al. |
| 8,521,280 | B2 | 8/2013 | Levin et al. |
| 9,008,769 | B2 | 4/2015 | Mika et al. |
| 9,320,903 | B2 | 4/2016 | Schwartz et al. |
| 9,333,352 | B2 | 5/2016 | Mika et al. |
| 9,370,661 | B2 | 6/2016 | Levin et al. |
| 9,370,662 | B2 | 6/2016 | Mika et al. |
| 9,427,586 | B2 | 8/2016 | Levin et al. |
| 9,526,900 | B2 | 12/2016 | Mika et al. |
| 9,656,086 | B2 | 5/2017 | Mika et al. |
| 9,687,636 | B2 | 6/2017 | Levin et al. |
| 9,731,136 | B2 | 8/2017 | Levin et al. |
| 9,878,162 | B2 | 1/2018 | Mika et al. |
| 2009/0118783 | A1 | 5/2009 | Patangay et al. |
| 2012/0215272 | A1 | 8/2012 | Levin et al. |
| 2013/0331901 | A1 | 12/2013 | Levin et al. |
| 2014/0128934 | A1 | 5/2014 | Schwartz et al. |
| 2014/0163600 | A1 | 6/2014 | Levin et al. |
| 2014/0163636 | A1 | 6/2014 | Levin et al. |
| 2014/0180353 | A1 | 6/2014 | Mika et al. |
| 2017/0113052 | A1 | 4/2017 | An et al. |
| 2017/0216599 | A1 | 8/2017 | Wisnoskey |
| 2017/0304048 | A1* | 10/2017 | Mika ................ A61N 1/36564 |
| 2019/0299004 | A1 | 10/2019 | Hahn et al. |

OTHER PUBLICATIONS

Israel, Carsten W., "Pacing-induced heart failure: should we avoid right ventricular pacing or not?f Parasympathetic", Europace (2017) 19, 165-168, doi:10.1093/europace/euw316.

Neizil, Petr, et al., "Pacemaker-Mediated Programmable Hypertension Control Therapy", J Am Heart Assoc. 2017;6: e006974. DOI: 10.1161/JAHA.117.006974, 1-14.

Neuzil, Petr, et al., "First-in-Man Study of a Pacemaker-Mediated Programmable Hypertension Control Therapy", ESC Congress, Clinical Trial Update Prevention Presentation, 18 pgs, Aug. 28, 2016.

"U.S. Appl. No. 16/366,937, Examiner Interview Summary dated Feb. 22, 2021", 2 pgs.

"U.S. Appl. No. 16/366,937, Non Final Office Action dated Dec. 22, 2020", 11 pgs.

"U.S. Appl. No. 16/366,937, Notice of Allowance dated May 17, 2021", 7 pgs.

"U.S. Appl. No. 16/366,937, Response filed Mar. 22, 2021 to Non Final Office Action dated Dec. 22, 2020", 11 pgs.

"U.S. Appl. No. 16/366,937. Preliminary Amendment Filed Mar. 27, 2019", (7 pgs).

"International Application Serial No. PCT/US2019/024324, International Preliminary Report on Patentability dated Oct. 8, 2020", 8 pgs.

"International Application Serial No. PCT/US2019/024324, International Search Report dated Jun. 3, 2019", 5 pgs.

"International Application Serial No. PCT/US2019/024324, Written Opinion dated Jun. 3, 2019", 5 pgs.

"International Application Serial No. PCT/US2019/024347, International Preliminary Report on Patentability dated Oct. 8, 2020", 8 pgs.

"International Application Serial No. PCT/US2019/024347, International Search Report dated Jun. 6, 2019", 4 pgs.

"International Application Serial No. PCT/US2019/024347, Written Opinion dated Jun. 6, 2019", 6 pgs.

* cited by examiner

PACING-BASED HYPERTENSION THERAPY SAFETY

CLAIM OF PRIORITY

This application claims the benefit of priority under 35 U.S.C. § 119(e) of U.S. Provisional Patent Application Ser. No. 62/685,454, filed on Jun. 15, 2018, and U.S. Provisional Patent Application Ser. No. 62/650,260, filed on Mar. 29, 2018, each of which is herein incorporated by reference in its entirety.

TECHNICAL FIELD

This document relates generally to medical devices, and more particularly, but not by way of limitation, to systems, devices, and methods for pacing-based hypertension therapy safety.

BACKGROUND

Blood pressure is the pressure of circulating blood on the walls of blood vessels, and typically refers to the pressure in large arteries of the systemic system. When further specified, such as left ventricular (LV) pressure, etc., such pressure refers to the pressure in that physiologic component. Blood pressure is commonly expressed in terms of systolic pressure, the pressure during a heart contraction, and diastolic pressure, the pressure between heart contractions, each measured in millimeters of mercury (mmHg).

High blood pressure, or hypertension (HTN), is a risk factor for mortality, as well as other adverse medical events, including, for example, heart failure (HF), ischemia, arrhythmia, stroke, acute cardiac decompensation, organ failure, etc. High blood pressure can also be asymptomatic, where patients don't appreciate their condition until an adverse medical event occurs. Accordingly, it is important to monitor blood pressure information, such as to monitor or assess patient condition or status, including worsening or recovery of one or more physiologic conditions, or to supplement other detections or determinations. Moreover, it is important to reduce blood pressure.

SUMMARY

This document discusses, among other things, systems and methods to generate a first pacing waveform during a first pacing period and a second pacing waveform during a second pacing period, and alternate the first and second pacing periods to provide pacing-based hypertension therapy to a heart of a patient to reduce patient blood pressure, wherein the first pacing waveform has a first atrioventricular (AV) delay and the second pacing waveform has a second AV delay longer than the first AV delay. Physiologic information can be received from the patient, and one of the first or second pacing period for delivery to the patient can be determined using the received physiologic information.

An example (e.g., "Example 1") of subject matter (e.g., a system) may include: a stimulation circuit configured to generate a first pacing waveform during a first pacing period and a second pacing waveform during a second pacing period, and to alternate the first and second pacing periods to provide pacing-based hypertension therapy to a heart of a patient to reduce patient blood pressure, wherein the first pacing waveform has a first atrioventricular (AV) delay and the second pacing waveform has a second AV delay longer than the first AV delay; a signal receiver circuit configured to receive physiologic information from the patient; and an assessment circuit configured to determine one of the first or second pacing period for delivery to the patient using the received physiologic information.

In Example 2, the subject matter of Example 1 may optionally be configured such that the assessment circuit is configured to adjust the first or second pacing period using the received physiologic information.

In Example 3, the subject matter of any one or more of Examples 1-2 may optionally be configured such that the assessment circuit is configured to detect a patient condition using the received physiologic information, and to discontinue the first pacing period in response to a detected worsening patient condition.

In Example 4, the subject matter of any one or more of Examples 1-3 may optionally be configured such that the assessment circuit is configured to detect an arrhythmia of the patient using the received physiologic information, and to discontinue the first pacing period in response to a number of detected arrhythmias over a threshold time period.

In Example 5, the subject matter of any one or more of Examples 1-4 may optionally be configured such that the assessment circuit is configured to determine an arrhythmia metric of the patient using the received physiologic information, and to adjust the first or second pacing period using the determined arrhythmia metric.

In Example 6, the subject matter of any one or more of Examples 1-5 may optionally be configured such that the assessment circuit is configured to determine a heart failure metric of the patient using the received physiologic information, and to adjust the first or second pacing period using the determined heart failure metric.

In Example 7, the subject matter of any one or more of Examples 1-6 may optionally be configured such that the signal receiver circuit is configured to receive third heart sound (S3) information and fourth heart sound (S4) information from the patient, and the assessment circuit is configured to determine an indication of early-to-late ventricular-filling velocities (E/A ratio) using the S3 information and the S4 information, and to adjust the first or second pacing period using the determined E/A ratio.

In Example 8, the subject matter of any one or more of Examples 1-7 may optionally be configured such that the signal receiver circuit is configured to receive first heart sound (S1) information from the patient, and the assessment circuit is configured to determine an indication of long-term impact of the first pacing period to the patient using S1 information detected during the second pacing period, and to adjust the first or second pacing period using the determined indication of long-term impact.

In Example 9, the subject matter of any one or more of Examples 1-8 may optionally be configured such that the signal receiver circuit is configured to receive first heart sound (S1) information and second heart sound (S2) information from the patient, and the assessment circuit is configured to determine an S1 metric and an S2 metric for the patient over the first and second pacing periods, and to adjust the first or second pacing periods to reduce the S2 metric without reducing the S1 metric.

In Example 10, the subject matter of any one or more of Examples 1-9 may optionally be configured such that the assessment circuit is configured to, in response to the determined first or second pacing period, provide an indication to a user to adjust the pacing-based hypertension therapy to the patient.

An example (e.g., "Example 11") of subject matter (e.g., at least one machine-readable medium) may include instructions that, when performed by a medical device, cause the medical device to: generate a first pacing waveform during a first pacing period and a second pacing waveform during a second pacing period, and alternate the first and second pacing periods to provide pacing-based hypertension therapy to a heart of a patient to reduce patient blood pressure, wherein the first pacing waveform has a first atrioventricular (AV) delay and the second pacing waveform has a second AV delay longer than the first AV delay; receive physiologic information from the patient; and determine one of the first or second pacing period for delivery to the patient using the received physiologic information.

In Example 12, the subject matter of Example 11 may optionally be configured such that the instructions, when performed by the medical device, cause the medical device to: adjust the first or second pacing period using the received physiologic information.

In Example 13, the subject matter of any one or more of Examples 11-12 may optionally be configured such that the instructions, when performed by the medical device, cause the medical device to: detect a patient condition using the received physiologic information; and discontinue the first pacing period in response to a detected worsening patient condition.

In Example 14, the subject matter of any one or more of Examples 11-13 may optionally be configured such that the instructions, when performed by the medical device, cause the medical device to: detect an arrhythmia of the patient using the received physiologic information; and discontinue the first pacing period in response to a number of detected arrhythmias over a threshold time period.

In Example 15, the subject matter of any one or more of Examples 11-14 may optionally be configured such that the instructions, when performed by the medical device, cause the medical device to: determine an arrhythmia metric of the patient using the received physiologic information, and to adjust the first or second pacing period using the determined arrhythmia metric.

An example (e.g., "Example 16") of subject matter (e.g., a method) may include: generating, using a stimulation circuit, a first pacing waveform during a first pacing period and a second pacing waveform during a second pacing period, and alternating the first and second pacing periods to provide pacing-based hypertension therapy to a heart of a patient to reduce patient blood pressure, wherein the first pacing waveform has a first atrioventricular (AV) delay and the second pacing waveform has a second AV delay longer than the first AV delay; receiving, using a signal receiver circuit, physiologic information from the patient; and determining, using an assessment circuit, one of the first or second pacing period for delivery to the patient using the received physiologic information.

In Example 17, the subject matter of Example 16 may optionally be configured to include adjusting, using the assessment circuit, the first or second pacing period using the received physiologic information.

In Example 18, the subject matter of any one or more of Examples 16-17 may optionally be configured to include: detecting, using the assessment circuit, a patient condition using the received physiologic information; and discontinuing the first pacing period in response to a detected worsening patient condition.

In Example 19, the subject matter of any one or more of Examples 16-18 may optionally be configured to include: detecting, using the assessment circuit, an arrhythmia of the patient using the received physiologic information; and discontinuing the first pacing period in response to a number of detected arrhythmias over a threshold time period.

In Example 20, the subject matter of any one or more of Examples 16-19 may optionally be configured to include: determining, using the assessment circuit, an arrhythmia metric of the patient using the received physiologic information; and adjusting, using the assessment circuit, the first or second pacing period using the determined arrhythmia metric.

An example (e.g., "Example 21") of subject matter (e.g., a system or apparatus) may optionally combine any portion or combination of any portion of any one or more of Examples 1-20 to include "means for" performing any portion of any one or more of the functions or methods of Examples 1-20, or a "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Pacing-based hypertension (HTN) therapy has developed for patients having implanted dual-chamber pacemakers with transvenous leads, where alternating periods of pacing at shorter and longer atrioventricular (AV) delay intervals has been shown to reduce blood pressure and thus help with hypertension. Pacing at a shortened AV delay interval (e.g., 20-80 ms) in contrast to a normal or longer AV delay interval (e.g., 100-180 ms) can reduce ventricular filling time, stroke volume and accordingly, arterial pressure. However, over time, such reductions may trigger a baroreflex response, increasing total peripheral resistance (TPR), and eventually increasing blood pressure towards its original level. Transitioning between periods of shorter and longer AV delay intervals can modulate the baroreflex response of the patient, preventing an increase in pressure by activation of the autonomic nervous system (ANS). Patterned-pacing-based HTN therapy can include interjecting longer AV delay intervals (e.g., 1-3 beats of normal or longer AV delay intervals) within the reduced AV delay periods (e.g., every 8-12 beats of shortened AV delay intervals) can further modulate the baroreflex response of the patient, further reducing transients after transitions, and drift between transitions.

Figure 1A:
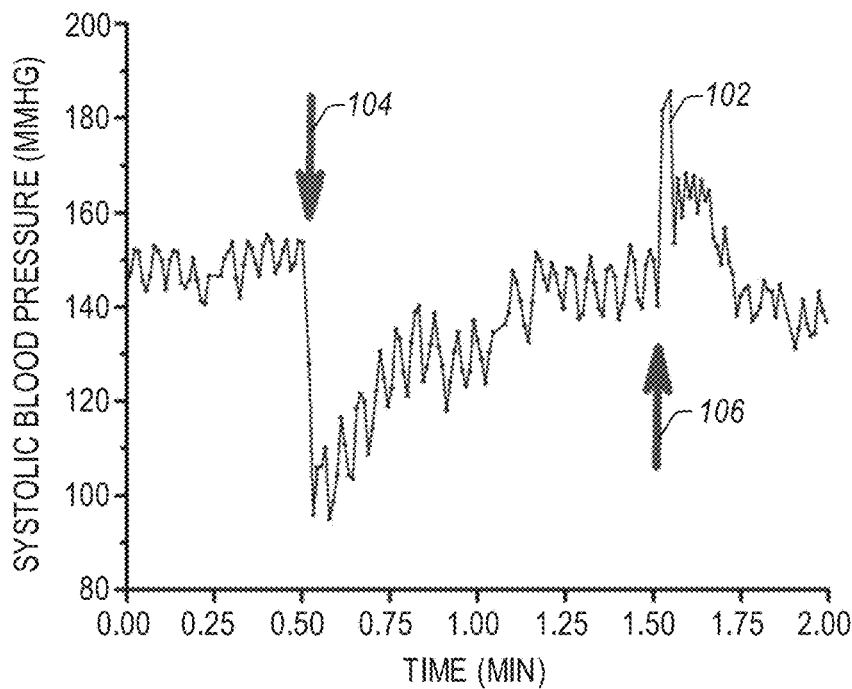
FIGS. 1A and 1B illustrate example relationships of systolic blood pressure measurements at different pacing patterns.
Figure 1B:
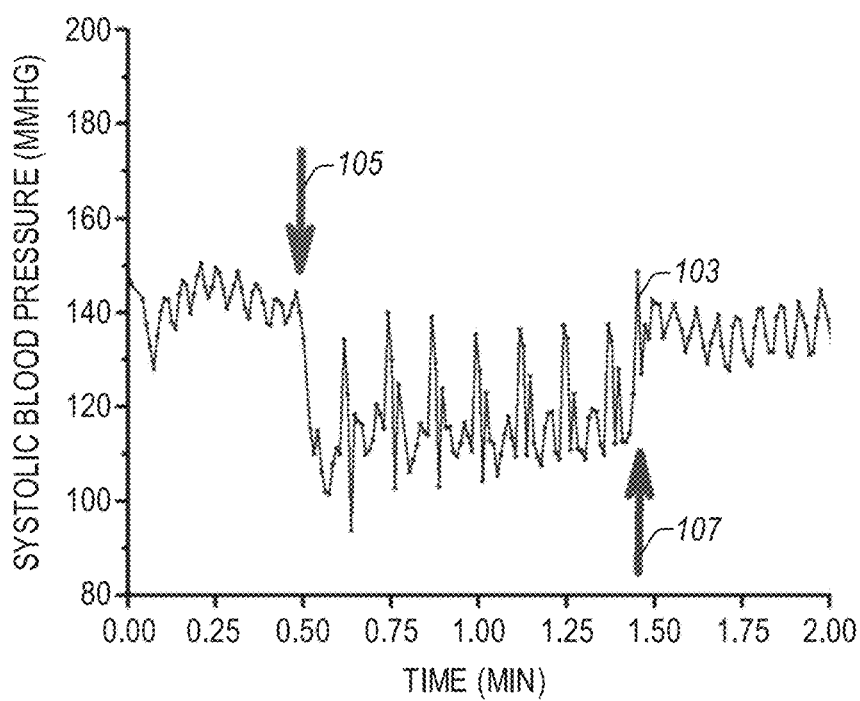

FIGS. 1A and 1B illustrate example relationships 100, 101 of systolic blood pressure measurements 102, 103 at different pacing patterns. In FIG. 1A, a first transition 104 in a pacing-based HTN therapy marks a change from a longer AV delay period (e.g., 140 ms AV delay intervals) to a shortened AV delay period (e.g., 40 ms AV delay intervals), where the systolic blood pressure 102 drops (e.g., from 150 mmHg to 100 mmHg) before rising to a level near the original pressure measurement. A second transition 106 marks a change from the shortened AV delay period (between first and second transitions 104, 106) back to the longer AV delay period (before and after the first and second transitions 104, 106), which causes a spike in the systolic blood pressure, then a return towards the baseline.

In FIG. 1B, a first transition 105 in a pattern-pacing-based HTN therapy marks a change from a longer AV delay (e.g., 140 ms) to a repeating sequence of 10 shortened AV delay (e.g., 40 ms) beats and 2 longer AV delay beats, and a second transition 107 marks a change from the repeating sequence in the shortened AV delay period (between first and second transitions 105, 107) to the longer AV delay period (before and after the first and second transitions 105, 107). In contrast to FIG. 1A, there are no significant drops or spikes in systolic blood pressure 103 after the first or second transition 105, 107, or significantly drift between the first and second transitions 105, 107, in the example illustrated in FIG. 1B.

The present inventors have recognized, among other things, improvements to pacing-based or pattern-pacing-based HTN therapy configured to increase safety or control, reduce detrimental impact, or improve cardiac function associated with the pacing-based HTN therapy, such as through assessment of physiologic information (e.g., heart sound information, etc.), and not rigid adherence to a predefined pattern or range. Such improvements allow the pacing-based or pattern-pacing-based HTN therapy to be optimized for each patient in a population, providing a greater benefit to the patient, and improved device function.

Ambulatory medical devices, including implantable, leadless, or wearable medical devices configured to monitor, detect, or treat various cardiac conditions associated with a reduced ability of a heart to sufficiently deliver blood to a body, such as heart failure (HF), arrhythmias, hypertension, etc. Various ambulatory medical devices can be implanted in a patient's body or otherwise positioned on or about the patient to monitor patient physiologic information, such as heart sounds, respiration (e.g., respiration rate, tidal volume, etc.), impedance (e.g., thoracic impedance), pressure, cardiac activity (e.g., heart rate (HR)), physical activity, posture, or one or more other physiologic parameters of a patient, or to provide electrical stimulation or one or more other therapies or treatments to optimize or control contractions of the heart.

Traditional cardiac rhythm management (CRM) devices, such as pacemakers, defibrillators, or cardiac monitors, include implanted devices (e.g., implantable cardioverter-defibrillators (ICDs), etc.), subcutaneous devices (e.g., subcutaneous ICDs (S-ICDs), etc.), or one or more other devices configured to be implanted within in a chest of a patient, or under the skin of the patient, in certain examples, having one or more leads to position one or more electrodes or other sensors at various locations in the heart, such as in one or more of the atria or ventricles. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from, or provide one or more therapies or stimulation to, the patient, for example, using one or more stimulation circuits.

Leadless cardiac pacemakers (LCP) include small (e.g., smaller than traditional implantable CRM devices), self-contained devices configured to detect physiologic information from or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

Wearable or external medical sensors or devices can be configured to detect or monitor physiologic information of the patient without required implant or an in-patient procedure for placement, battery replacement, or repair. However, such sensors and devices, in contrast to implantable, subcutaneous, or leadless medical devices, may have reduced patient compliance, increased detection noise, or reduced detection sensitivity.

Determination of one or more patient conditions (e.g., hypertension, HF, etc.), or risk stratification for one or more patient conditions, often requires some initial assessment time to establish a baseline level or condition from one or more sensors or physiologic information from which a detected deviation is indicative of the patient condition, or risk of patient condition or future adverse medical event (e.g., the risk of the patient experiencing a heart failure event (HFE) within a following period, etc.). Changes in physiologic information can be aggregated and weighted based on one or more patient-specific stratifiers. However, such changes and risk stratification are often associated with one or more thresholds, for example, having a clinical sensitivity and specificity across a target population with respect to a specific condition (e.g., HF), etc., and one or more specific time periods, such as daily values, short-term averages (e.g., daily values aggregated over a number of days), long-term averages (e.g., daily values aggregated over a number of short-term periods or a greater number of days (sometimes different days than used for the short-term average)), etc.

For example, a multisensor algorithm has been demonstrated to predict HF events in patients with a high sensitivity and low false positive rate using physiologic information detected from one or more implanted or ambulatory medical devices. In other examples, such algorithm can be applied to one or more other medical events, such as hypertension or one or more conditions associated with hypertension, etc. The multisensor algorithm can determine a composite physiologic parameter using one or more of the following physiologic information: heart sounds (e.g., a first heart sound (S1), a second heart sound (S2), a third heart sound (S3), a fourth heart sound (S4), heart-sounds related time intervals, etc.), thoracic impedance (TI), respiratory rate (RR), rapid shallow breathing index (RSBI), heart rate (HR) (e.g., nighttime HR), activity, posture, cardiac activity, pressure, etc.

In certain examples, such multisensor algorithm can be adjusted using a determined patient risk level (e.g., a stratifier). The combination of or weight of respective primary and secondary sensors used to determine the composite physiologic parameter can be adjusted using the determined patient risk level. For example, if the determined patient risk level indicates a low risk of a worsening physiologic condition, the composite physiologic parameter can be determined using one or more primary sensors (and not one or more secondary sensors). If the determined patient risk level indicates a medium or high risk of worsening heart failure, the composite physiologic parameter can be determined using the primary sensors and a combination of the secondary sensors, depending on the determined patient risk level.

Figure 2:
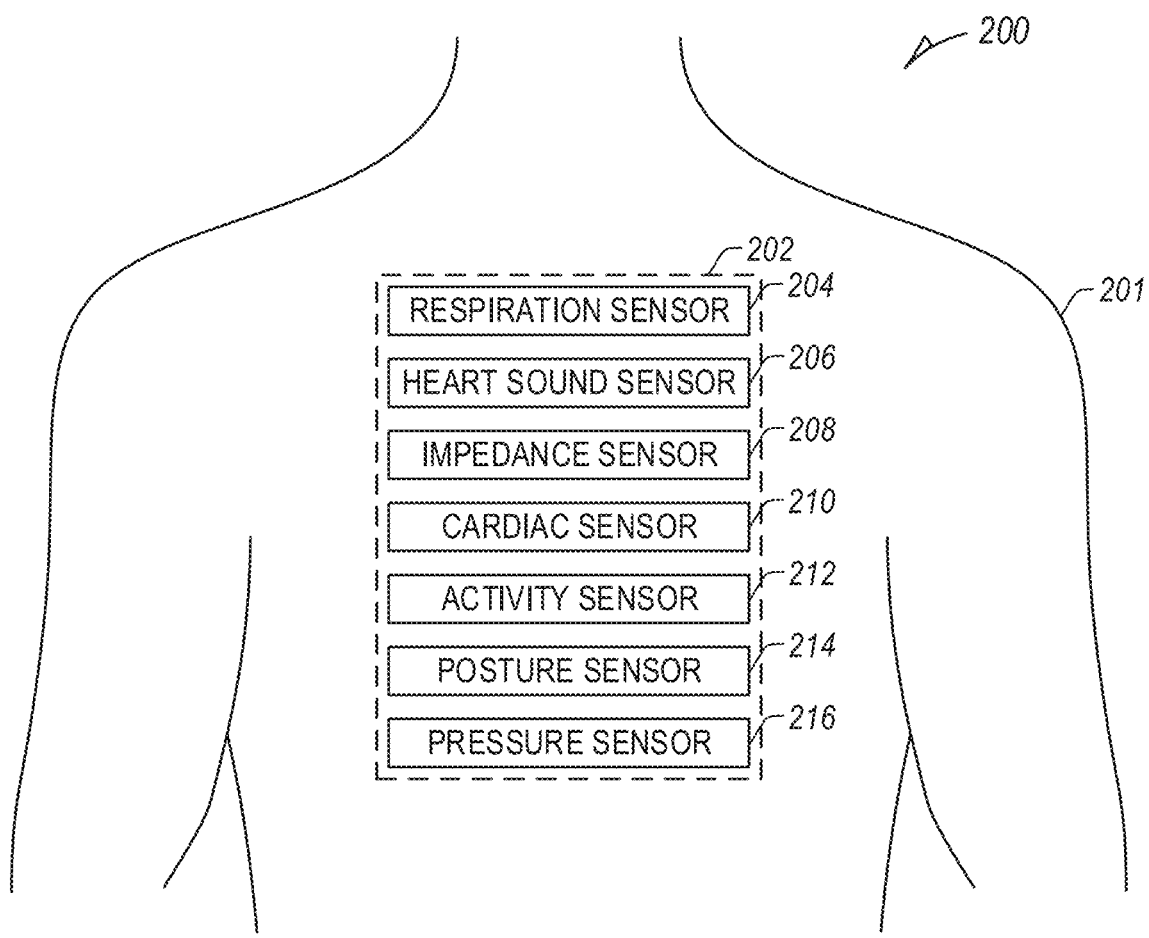
FIG. 2 illustrates an example system including an ambulatory medical device (AMD) configured to sense or detect information from a patient.

FIG. 2 illustrates an example system 200 including an ambulatory medical device (AMD) 202 configured to sense or detect information from a patient 201. In an example, the AMD 202 can include an implantable medical device (IMD), a subcutaneous or leadless medical device, a wearable or external medical device, or one or more other implantable or external medical devices or patient monitors. The AMD 202 can include a single device, or a plurality of medical devices or monitors configured to detect patient information.

The AMD 202 can include one or more sensors configured to receive physiologic information of a patient 201. In an example, the AMD 202 can include one or more of a respiration sensor 204 configured to receive respiration information (e.g., a respiration rate (RR), a respiration volume (tidal volume), etc.), a heart sound sensor 206 configured to receive heart sound information, an impedance sensor 208 (e.g., intrathoracic impedance sensor, transthoracic impedance sensor, etc.) configured to receive impedance information, a cardiac sensor 210 configured to receive cardiac electrical information, an activity sensor 212 configured to receive information about a physical motion (e.g., activity, steps, etc.), a posture sensor 214 configured to receive posture or position information, a pressure sensor 216 configured to receive pressure information, or one or more other sensors configured to receive physiologic information of the patient 201.

One or more of the sensors in the AMD 210 may include existing physiologic sensors. However, using the system and methods described herein, the sensitivity and specificity of one or more metrics associated with a risk of worsening heart failure (HF) detected using existing sensors can be increased without otherwise increasing system cost or power, or negatively affecting usable battery life of the existing sensors.

Safety

The present inventors have recognized, among other thing, that right ventricle (RV) pacing, such as continuous RV pacing, can lead to pacing-induced heart failure (HF), such as ventricular dyssynchrony (e.g., interventricular asynchrony, intraventricular asynchrony, etc.). In certain examples, dyssynchrony can lead to an enlarged heart that must work harder to provide required cardiac output due to uncoordinated contractions.

In an example, a composite physiological parameter can be used to monitor a patient for worsening HF or one or more other physiologic conditions. The composite physiological parameter can be adjusted by a stratifier, such as described above. In certain examples, S3 can be related to filling pressure—an increase in S3 amplitude, morphology, or energy (e.g., an integral or RMS value of S3 over an S3 window, in certain examples, determined with respect to one or more other heart sounds, such as S2, or cardiac activity, such as one or more cardiac features (e.g., R-wave, etc.), heart rate, etc.) can be indicative of an increase in filling pressure. An increase in filling pressure can be indicative of HF. In other examples, an increase in S3 (e.g., >1 mG, if measured with an accelerometer), respiration rate trending (RRT) (e.g., >20 BPM), or an increase in RRT variability (e.g., max−min>4 bpm) can be indicative of HF.

In an example, one or both of the composite physiological parameter or the stratifier can include or be substantially based on the S3 amplitude, morphology, energy, a differential between two S3 values taken at different times or over different intervals (e.g., short-term average (or median or one or more other values) versus long-term average (or medium or one or more other values), having overlapping or non-overlapping windows, etc.), or an S3 value normalized with one or more other measures (e.g., S1 (related to contractility, inotropy, cannon-wave back pressure, etc.), S2 (related to blood pressure in the aorta, ejection fraction, etc.), S3 (e.g., fluid backup, etc.), S4, etc.). In an example, S2/S1, S3/S1, S3/S4, or one or more other normalized heart sound values can be used, or one or more other values normalized by a heart sound (e.g., S3). In other examples, one or more other heart sounds can be determined.

In certain examples, S4 can be detected without coordinating or lining up the electrical cardiac activity to accelerometer information used to determine heart sounds, etc. The ratio of S3/S4 can be used as a surrogate for the ratio of early (E) to late (A) ventricular filling velocities (E/A ratio). The E/A ratio can be used, alone or in combination with other physiologic parameters, to determine a possible risk of adverse outcome of pacing-based or pattern-pacing-based HTN therapy. For example, during therapy, if S1 is high (e.g., at or above a baseline level (e.g., 2 mG, etc.) or increasing relative to a previous S1 level or to an S1 level outside of therapy (e.g., 10% higher than an S1 level outside of therapy, etc.), indicative of a threshold amount of ventricular filling and contraction), therapy can continue. If S1 is low (e.g., below a baseline level or decreasing relative to a previous S1 level or to an S1 level outside of therapy (e.g., 10% lower than an S1 level outside of therapy, etc.)), a ratio of S3/S4 can be determined. If the ratio of S3/S4 is low and S3 is low (e.g., below baseline levels (e.g., an S3/S4 ratio below 0.8, etc., or an S3 level below 1 mG, etc.) or decreasing relative to previous levels or previous levels outside of therapy, indicative of less ventricular filling and a smaller amount of filling from passive ventricular filling), pacing-based or pattern-pacing-based HTN therapy may proceed, though with caution, while monitoring for changes (e.g., chronic changes in absolute or relative levels) in S1 or S3. If the ratio of S3/S4 ratio is low and S3 is high (e.g., with respect to baseline levels or relative to previous levels or previous levels outside of therapy, indicative of less filling but a significant portion of which comes from atrial kick), pacing-based or pattern-pacing-based HTN therapy can be discontinued.

Thus, one or more of pacing-based or pattern-pacing-based HTN therapy can be adjusted, reduced, or discontinued using an increase in detected S3 (or one or more other heart sound parameters), or an increase in a composite physiological parameter (or stratifier) determined using, or based on, S3 (or one or more other heart sound parameters). For example, a significant increase in S3 (e.g., relative to a previous value, such as a 20% increase, etc.), may indicate that LV filling pressure has increased and not enough blood has been cleared from pulmonary circulation, and that pacing-based or pattern-pacing-based HTN therapy should be discontinued. In other examples, pacing-based or pattern-pacing-based HTN therapy can be adjusted, reduced, or discontinued to maintain or reduce an S3 value, or a composite physiological value or stratifier determined using or based on an S3 value (or one or more other heart sound parameters). In other examples, a diminishing S2 relative to an S2 level outside of therapy or relative to intrinsic beats at the start of therapy can indicate an effective therapy. Accordingly, pacing-based or pattern-pacing-based HTN therapy can be adjusted to maintain S1, but diminish S2. In an example, one or more other physiologic parameters can be used, alone, in combination with one or more other parameters (e.g., S3, S4, etc.), or as part of a composite physiologic parameter or stratifier, to adjust or provide a therapy.

In other examples, one or more heart sound parameters can be used to determine if hypotension occurs during therapy. For example, blood pressure can be detected using S2 in the absence of substantive changes in S1 indicative of contractility changes. In other examples, one or more other types of information can be used to determine if the patient has fallen, or is suffering from low blood pressure, such as identifying accelerometer or activity data indicative of gate changes, falls, decreases in activity, or one or more other indications of low blood pressure. If hypotension is determined, the pacing-based or pattern-pacing-based HTN therapy can be discontinued. In other examples, upon determination of hypotension, the pacing rate, AV delay value, or one or more other pacing parameters can be adjusted to increase blood pressure. For example, using one or more Frank-Starling relationships, a pacing parameter can be adjusted to increase blood pressure (e.g., increasing filling time, etc.). Moreover, such relationships can be detected, and parameters controlled, using heart sound information.

In certain examples, in patients without significant atrial kick, an amount of atrial filling must occur before activation to provide sufficient cardiac output. Such patients may not tolerate a shortened AV delay. In certain examples, diastolic filling parameters and atrial kick can be detected using heart sounds. For example, an increase in S1 can be indicative of an increased diastolic filling, and a decrease in S1 can be indicative of a decreased diastolic filling. In another example, an S2-R or an S4-R interval may be used to quantify diastolic filling time. Patients with S2-R intervals below a threshold (e.g., <300 msec) may not be good candidates for pacing-based or pattern-based therapy, due to a lack of passive filling. In such cases, active filling time may be more beneficial than maintaining metabolic demand. Such measures can be monitored during therapy as a safety precaution.

Further, atrial kick can be detected using S4. In other examples, physiologic information can be monitored to detect retrograde conduction or changes to an intrinsic P-R interval, related to diastolic filling time. Further, identifying a split S1 or a split S2 may indicate that a patient may not tolerate a shortened AV delay. Patients can be screened prior to pacing-based or pattern-pacing-based HTN therapy using a detected or identified split S1 or split S2. In other examples, pacing-based or pattern-pacing-based HTN therapy can be adjusted, reduced, or discontinued using a detected atrial kick, split S1 or split S2, or detected diastolic filling parameters. In an example, pacing-based or pattern-pacing-based HTN therapy can be intermittently suspended, with one or more heart sound measurements taken during the break in therapy (e.g., during a time with longer AV delay intervals, etc.). For example, S1 measurements, or a composite physiological parameter or stratifier can be determined using or based on S1, can be determined to evaluate a long-term impact of pacing-based or pattern-pacing-based HTN therapy. For example, S1 can be used to provide an indication of cardiac contractility. A significant drop in S1 (e.g., relative to previous levels) may indicate a reduction in contractility. If S1 cannot be maintained or increased, pacing-based or pattern-pacing-based can be discontinued.

In other examples, pacing-based or pattern-pacing-based HTN therapy, transitioning between a longer AV delay interval and a shortened AV delay interval, or pacing with shortened AV delay intervals may lead to arrhythmias. Accordingly, a composite physiologic parameter, stratifier, or other physiologic parameter can be monitored to reduce number of transitions between longer AV delay intervals and shortened AV delay intervals to provide a desired blood pressure decrease, thereby reducing the risk of arrhythmias. Further, physiologic information can be monitored for signs of arrhythmias, such as premature contractions (PACs), atrial arrhythmia burden, or one or more other arrhythmias. Pacing-based or pattern-pacing-based HTN therapy can be adjusted, reduced, or discontinued using a number of detected arrhythmias within a certain time period.

In an example, instead of pacing at the RV, pacing-based or pattern-pacing-based HTN therapy can be implemented using His-bundle pacing, such as providing a pacing pulse configured to activate the His bundle, bundle branches, or Purkinje fibers at or near the atrioventricular (AV) node in the right atrium (RA) to preserve synchronous ventricular depolarization without separate pacing in the RV. His-bundle pacing may provide a single-lead solution, sensing the RA and pacing the His bundle using a single lead in the RA, and activating the His bundle using a pulse configured to capture both of a His bundle and the local myocardium, or to capture the His bundle and not the local myocardium.

Control

In an example, one or more of the specific patterns of longer and shorter AV delay period (e.g., 8 shortened AV delay interval beats then 2 longer AV delay interval beats in a shortened AV delay period, etc.) of pacing-based or pattern-pacing-based HTN therapy, or the value of the AV delay intervals of the longer AV delay and the shortened AV delay, can be individually controlled, determined, or optimized for a specific patient, using patient-specific physiologic information, such as detected from the patient by one or more ambulatory medical devices. In an example, the physiologic information can include a composite physiological parameter, a stratifier configured to adjust the composite physiologic parameter, or other physiologic information, including (or based on) one or more heart sounds (e.g., one or more of S1-S4, etc.), impedance (e.g., thoracic impedance, etc.), or one or more other physiologic parameter, etc. Moreover, such previously determined patterns or values may change over time, and in certain examples, can be optimized for specific time periods or other patterns, or triggered with respect to one or more other physiologic information (e.g., sleep, exercise, time of day, etc.).

In an example, the device may evaluate the S1 and S2 response to a specific pacing protocol to determine the value of the shorter and longer AV delay intervals for a specific patient. In certain examples, the pacing protocol may involve testing a shortened AV delay interval immediately following an intrinsic beat and evaluating the S1 and S2 changes during the shortened AV delay beat relative to the preceding intrinsic beat. Shortening of the AV delay is expected to increase S1 and reduced S2 amplitudes. The value of the shortened AV delay can be successively reduced such that at each successive step transitions from an intrinsic beat to a progressively shorter AV delay as compared to previous transition. An optimal shortened AV delay can include an AV delay beyond which increase in S1 amplitude, or decrease in S2 amplitude or both, relative to corresponding values during the preceding intrinsic beat is similar to the changes during the previous transition to a slightly longer shortened AV delay. An optimal shortened AV delay can include an AV delay at which further reduction in AV delay are not expected to cause further changes in heart sound based metrics (e.g., an increase in S1 or decrease in S2, or both, etc.) relative to a preceding intrinsic beat (e.g., a point of diminishing returns).

Once the shortened AV delay is optimized, the pacing protocol can test multiple options for longer AV delay. Each test can start from an intrinsic beat followed by 8-12 beats at the optimal shortened AV delay followed by 1-3 beats of one particular longer AV delay being evaluated. Various values of longer AV delay can be evaluated successively. Optimality of the longer AV delay can be determined using maximal reduction of S2 amplitude averaged over multiple beats 2-3 minutes from the initial intrinsic beat or minimal change in S2 amplitude (e.g., averaged over multiple beats 2-3 minutes from the initial intrinsic beat) from the first few shortened AV delay beat following the intrinsic beat. Once the two AV delays are optimized, they can be used for the particular subject until a need for re-optimization arises.

Further, S2 can be used to determine an optimal pattern during a shortened AV delay period. For example, after a transition from the longer AV delay period to the shortened AV delay period, shortened AV delay intervals can continue until S2 (or a composite value or stratifier including or based on S2) exceeds or increases above a threshold relative to an S2 value prior to transition (e.g., a relative change, such as 20%, etc.), in certain examples in combination with a heart rate increase above a threshold relative to a heart rate prior to transition (e.g., a relative change, such as 20%, etc.), before injecting 1-2 longer AV delay intervals. In an example, the number of longer AV delay intervals can be determined using S2 information, heart rate information, or a combination of (or composite or stratifier including or based on) both. In the shortened AV delay period, longer AV delay intervals can be periodically injected to keep the S2 information, heart rate information, or a combination of (or composite or stratifier including or based on) both, below one or more thresholds.

In an example, heart sound information may require signal averaging over several periods of a pattern (e.g., ensemble averaged heart sounds, etc.). In an example, the value of the AV delay intervals in the AV delay periods can be separately averaged (e.g., for a longer AV delay period or a shortened AV delay period, etc.) across various overlapping, or non-overlapping timer periods.

In other examples, a cannon A wave (a RA/LA contraction against a closed tricuspid valve/mitral valve) can be detected using S1 information. In an example, the shortened AV delay can be successively lowered until a cannon A wave is detected. Once detected, the shortened AV delay interval can be set as some percentage (e.g., 90%, etc.) of the cannon A wave value.

In other examples, the upper bound of the AV delay can be determined using a P wave of a cardiac signal and S4 information (e.g., a P-S4 time). The shortened AV delay can be set as the determined upper bound (e.g., the P-S4 time). Further, as S4 can represent a mechanical contraction, the shortened AV delay can be set shorter than the upper bound of the AV delay, but longer than the end of S4 timing, so as not to affect atrial contraction.

In other examples, stroke impedance can be determined using a detected impedance. In certain examples, impedance information can be filtered for respiration information, minute ventilation (MV) information, or one or more other impedance measurements, depending on selected impedance vectors. In an example, a cardiac component of detected MV information can be used to confirm HS information, or can be used as an independent metric. The shortened AV delay intervals can be reduced, and the longer AV delay intervals can be increased, e.g., until stroke impedance falls below an absolute or relative threshold value, or until a further reduction in AV delay would no longer lead to any reduction in stroke impedance (e.g., a point of diminishing returns).

Exercise Capacity and Tolerance

Shortening AV delay intervals to reduce filling and pressure may also reduce cardiac output, which can negatively impact exercise capacity and, in certain examples, patient tolerance to a provided therapy. The patient may feel the alternating patterns (e.g., a longer AV delay interval versus a shortened AV delay interval, a transition back to the longer AV delay interval from the shorter AV delay, etc.) of the pacing-based or pattern-pacing-based HTN therapy, and such feeling may be unpleasant.

In an example, information from one or more sensors (e.g., impedance, respiration, activity, posture, etc.) can be used to adjust, reduce, or discontinue pacing-based or pattern-pacing-based HTN therapy based on patient activity, exercise, or required cardiac output. If the patient is detected as active, therapy can be suspended or altered less drastically, such as to retain cardiac output.

In certain examples, if cardiac output is required, but heart rate does not rise, the vasculature of the heart can change, and the heart can try to pump harder, which can be measured using heart sounds (e.g., S1, S2, etc.). If activity is detected and blood pressure increases (e.g., such as indicated by heart sounds, etc.), but the heart rate does not rise (e.g., at the same time or to the same degree) with the detected activity, a pacing rate can be increased to improve cardiac output, in certain examples, separate from, or in combination with modulating of an AV delay or pacing pattern. Once activity is detected, an assessment circuit can switch modes, from pacing-based or pattern-pacing-based HTN therapy mode to an activity mode, where an increased cardiac output is desired. Once the activity mode is triggered, some hysteresis can be required to transition back to the pacing-based or pattern-pacing-based HTN therapy mode. In certain examples, no hysteresis is required to transition back to the activity mode.

In certain examples, an increase in heart sounds (e.g., S1-S4) can be used to adjust one or more of a pattern or an AV delay value. In an example, information from one or more sensors (e.g., impedance, respiration, activity, posture, etc.) can be combined with heart sounds to control blood pressure control and exercise capacity.

In an example, the transition between the longer AV delay period and the shortened AV delay period can be gradual, stepping between the shortened AV delay period and the longer AV delay period in a number of steps to reduce abrupt changes, and thereby reduce unpleasant sensations associated with abrupt changes in AV delay, and reducing the likelihood for baroreflex response. For example, the AV delay can be stepped down by a specific amount (e.g., 2 ms, 5 ms, 10 ms, etc.), in certain examples, no more than a threshold amount each beat. In other examples, changes in AV delay intervals or the AV delay patterns can be synchronized, altered, or controlled with respect to a detected respiration cycle. For example, a heart rate can be driven up and an AV delay interval can be increased during late inhalation, while, in contrast, the heart rate can be lowered and the AV delay interval can be decreased during expiration.

Hypertension patients can be divided into different groups of overnight responders: dippers and non-dippers. Many patients, when monitored for periods 24-hours or longer, show lower blood pressure measurements at night. Such patients are referred to as "dippers". In contrast, patients that present constant or near-constant blood pressure measurements at day or night are referred to as "non-dippers". Non-dippers generally have worse outcomes. In an example, pacing-based or pattern-pacing-based HTN therapy can alter an AV delay or provide a pacing pattern configured to promote a natural diurnal pattern, in certain examples, turning a non-dipper into a dipper. In other examples, a ventricle can be paced to detune the contraction, resulting a reduced cardiac output, which can be used to promote a natural diurnal pattern.

In an example, one or more sensors disclosed herein can be used to determine if the patient is sleeping (e.g., activity sensor, posture sensor, etc.), such as to distinguish between daytime and nighttime blood pressure measurements. In other examples, information about the sleep state of the patient can be received from the patient or a caregiver, such as at setup of the ambulatory medical device, or information about the sleep state of the patient can be assumed at specific times of day, in certain examples confirmed using information from the one or more sensors. In an example, the pacing-based or pattern-pacing-based HTN therapy can be more aggressive (e.g., longer time periods of (more) shortened AV delays, shorter AV delay values, etc.) when the patient is sleeping, inactive, or at rest, due to the decrease in required patient cardiac output.

In certain examples, when a patient is detected as in atrial fibrillation (AF), altering a V-V pattern (e.g., in a ventricular rate regularization (VRR) mode of an ambulatory medical device) can alter a blood pressure in a patient. In other examples, information about heart sounds can be used to automatically adjust or optimize rate response of a therapy. For example, if S1 (e.g., S1 amplitude, morphology, or energy) increases at a given heart rate, the rate response factor of the VRR mode can be increased to increase heart rate. Similarly, to reduce heart rate, the rate response factor of the VRR mode can be decreased (e.g., to pace more intermittently).

In certain examples, an assessment circuit can propose changes to a clinician, for example, AV delay values, pacing patterns, pacing rate increases, etc., as many times clinicians program devices too conservatively. The proposed changes can enable a clinician to provide patient benefit they may not otherwise feel comfortable immediately doing so. The decrease in time to proper device programming can provide a substantive benefit to the patient. In other examples, the assessment circuit can make changes to the programming of an ambulatory medical device (e.g., within pre-approved safety bounds, etc.) configured to provide a therapy to the patient.

Increased Pacing Rate

In certain examples, as AV delay intervals are shortened in pacing-based or pattern-pacing-based HTN therapy, the pacing rate can be increased to account for the reduced cardiac output of the shortened AV delay intervals, separate from or in conjunction with detecting patient activity. In an example, the pacing rate increases can be implemented with each shortened AV delay intervals. In other examples, the pacing rate increases can be implemented with shortened AV delay intervals at specific times (e.g., during activity, during the day, while moving or taking steps, etc.) and not others (e.g., while inactive, sitting, sleeping, lying down, etc.).

In an example, the pacing rate increase can be implemented during some or all of each shortened AV delay period. In certain examples, the pacing rate can increase by a percentage, a threshold, or a set amount (e.g., 10%, 10-20 bpm, etc.). When increasing the pacing rate, one or more physiologic parameters (e.g., heart sounds S1-S4, stroke volume, etc.), composite physiologic parameters, or stratifiers can be monitored to ensure the cardiac output is increasing. As cardiac output (CO) is related to heart rate and stroke volume, care must be taken to ensure that, as one parameter is changed, others behave as desired. In an example, physiologic information from the patient can be used to modulate the pacing rate increase, such as using heart sounds, cardiac electrical activity, respiration information, impedance, activity, etc. The pacing rate changes can be abrupt, switching between rates, or gradual, stepping between rates so that the patient does not feel the transitions.

In an example, in a pattern-pacing-based HTN therapy, including 8-12 beats of shortened AV delay intervals interjected with 1-3 beats of longer AV delay intervals, the pacing rate can either stay at the increased value throughout the shortened AV delay period (including the 1-3 beats of longer AV delay interval), transitioning back to the previous pacing rate at the transition to the longer AV delay period, or the pacing rate can modulate as the shortened AV delay intervals are interjected with the longer AV delay intervals, with the rate transitioning back or towards the previous rate at each interjected longer AV delay interval.

Control Parameters

In an example, once pattern-pacing therapy begins, a number of conditions can be monitored, in conjunction with or separate from one or more physiologic parameters from the patent.

At a first step, an assessment circuit can determine whether an arrhythmia is present, for example, using received physiologic information from the patient. The assessment circuit can monitor an atrial rate of the patient, as well as activity and respiration information (e.g., accelerometer signal and minute ventilation signal, such as using an impedance sensor, etc.).

At a second step, optionally concurrent with the first step, the patterned-pacing therapy can be modulated using one or more physiologic parameters (e.g., heart sounds S1-S4, stroke volume, etc.), or one or more composite physiologic parameters or stratifiers. In an example, the assessment circuit can recommend changes to one or more AV delay intervals (e.g., a shortened AV delay interval, a longer AV delay interval, etc.), or moreover, can recommend a number of different patterns (e.g., X shortened AV delay intervals followed by Y longer AV delay intervals, repeating with those or updated values, for a certain time period, depending on the physiologic parameters or one or more composite physiologic parameters or stratifiers.

At a third step, optionally concurrent with one or more of the first and second steps, long-term safety monitoring or one or more other conditions can be monitored (e.g., dyssynchrony, arrhythmia, exercise or activity, etc.).

In an example, depending on the output of the first and second steps, if nothing arises to cause concern, the first and second steps can loop while continuing to provide patterned-pacing therapy. At a fourth step, the pattern-pacing therapy is stopped, in certain examples, in response to received physiologic information or because the therapy is complete.

Figure 3:
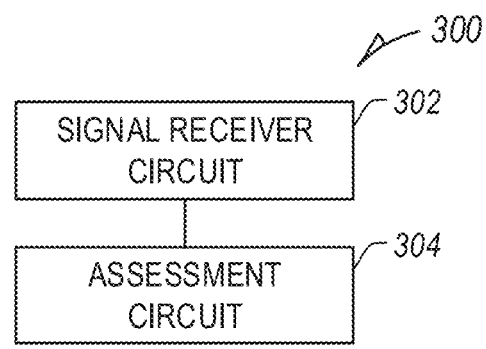
FIG. 3 illustrates an example system (e.g., a medical device, etc.) including a signal receiver circuit and an assessment circuit.

FIG. 3 illustrates an example system (e.g., a medical device, etc.) 300 including a signal receiver circuit 302 and an assessment circuit 304. The signal receiver circuit 302 can be configured to receive patient information, such as physiologic information of a patient (or group of patients) from one or more sensors. The assessment circuit 304 can be configured to receive information from the signal receiver circuit 302, and to determine one or more parameters (e.g., composite physiologic parameters, stratifiers, one or more pacing parameters, etc.), such as described herein.

The assessment circuit 304 can be configured to provide an output to a user, such as to a display or one or more other user interface, the output including a score, a trend, or other indication. In other examples, the assessment circuit 304 can be configured to provide an output to another circuit, machine, or process, such as to control, adjust, or cease a therapy of a medical device, etc.

Figure 4:
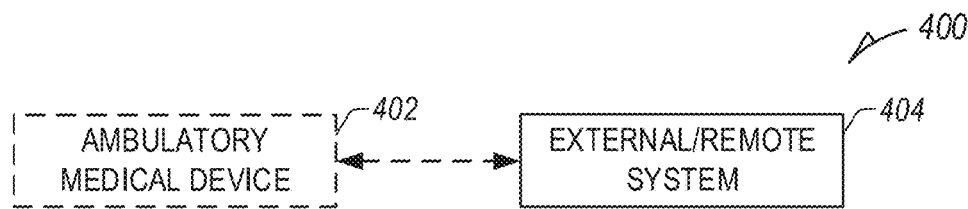
FIG. 4 illustrates an example system including an ambulatory medical device (AMD) coupled to an external or remote system, such as an external programmer.

FIG. 4 illustrates an example system 400 including an ambulatory medical device (AMD) 402 coupled to an external or remote system 404, such as an external programmer. In an example, the AMD 402 can be an implantable device, an external device, or a combination or permutation of one or more implantable or external devices. In an example, one or more of the signal receiver circuit 302 or the assessment circuit 304 can be located in the AMD 402, or the remote system 404. In an example, the AMD 402 can include a stimulation circuit configured to generate one or more pacing or defibrillation waveforms to be provided to a patient. The remote system 404 can include a specialized device configured to interact with the AMD 402, including to program or receive information from the AMD 402.

Figure 5:
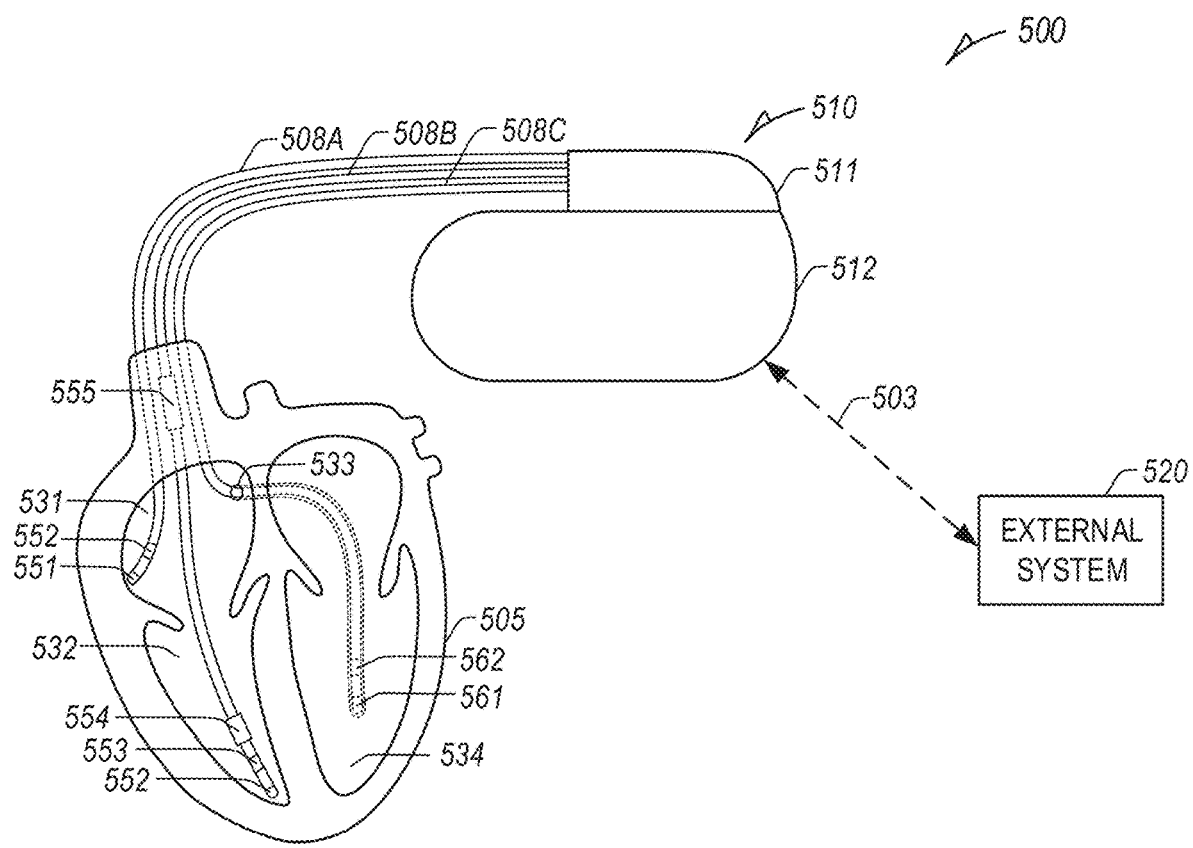
FIG. 5 illustrates an example of a Cardiac Rhythm Management (CRM) system and portions of an environment in which the CRM system can operate.

FIG. 5 illustrates an example of a Cardiac Rhythm Management (CRM) system 500 and portions of an environment in which the CRM system 500 can operate. The CRM system 500 can include an ambulatory medical device, such as an implantable medical device (IMD) 510 that can be electrically coupled to a heart 505 such as through one or more leads 508A-C coupled to the IMD 510 using a header 511, and an external system 520 that can communicate with the IMD 510 such as via a communication link 503. The IMD 510 may include an implantable cardiac device such as a pacemaker, an implantable cardioverter-defibrillator (ICD), or a cardiac resynchronization therapy defibrillator (CRT-D). The IMD 510 can include one or more monitoring or therapeutic devices such as a subcutaneously implanted device, a wearable external device, a neural stimulator, a drug delivery device, a biological therapy device, or one or more other ambulatory medical devices. The IMD 510 may be coupled to, or may be substituted by a monitoring medical device such as a bedside or other external monitor.

As illustrated in FIG. 4, the IMD 510 can include a hermetically sealed can 512 that can house an electronic circuit that can sense a physiologic signal in the heart 505 and can deliver one or more therapeutic electrical pulses to a target region, such as in the heart, such as through one or more leads 508A-C. In certain examples, the CRM system 500 can include only a single lead, such as 508B, or can include only two leads, such as 508A and 508B.

The lead 508A can include a proximal end that can be configured to be connected to IMD 510 and a distal end that can be configured to be placed at a target location such as in the right atrium (RA) 531 of the heart 505. The lead 508A can have a first pacing-sensing electrode 551 that can be located at or near its distal end, and a second pacing-sensing electrode 552 that can be located at or near the electrode 551. The electrodes 551 and 552 can be electrically connected to the IMD 510 such as via separate conductors in the lead 508A, such as to allow for sensing of the right atrial activity and optional delivery of atrial pacing pulses. The lead 508B can be a defibrillation lead that can include a proximal end that can be connected to IMD 510 and a distal end that can be placed at a target location such as in the right ventricle (RV) 532 of heart 505. The lead 508B can have a first pacing-sensing electrode 552 that can be located at distal end, a second pacing-sensing electrode 553 that can be located near the electrode 552, a first defibrillation coil electrode 554 that can be located near the electrode 553, and a second defibrillation coil electrode 555 that can be located at a distance from the distal end such as for superior vena cava (SVC) placement. The electrodes 552 through 555 can be electrically connected to the IMD 510 such as via separate conductors in the lead 508B. The electrodes 552 and 553 can allow for sensing of a ventricular electrogram and can optionally allow delivery of one or more ventricular pacing pulses, and electrodes 554 and 555 can allow for delivery of one or more ventricular cardioversion/defibrillation pulses. In an example, the lead 508B can include only three electrodes 552, 554 and 555. The electrodes 552 and 554 can be used for sensing or delivery of one or more ventricular pacing pulses, and the electrodes 554 and 555 can be used for delivery of one or more ventricular cardioversion or defibrillation pulses. The lead 508C can include a proximal end that can be connected to the IMD 510 and a distal end that can be configured to be placed at a target location such as in a left ventricle (LV) 534 of the heart 505. The lead 508C may be implanted through the coronary sinus 533 and may be placed in a coronary vein over the LV such as to allow for delivery of one or more pacing pulses to the LV. The lead 508C can include an electrode 561 that can be located at a distal end of the lead 508C and another electrode 562 that can be located near the electrode 561. The electrodes 561 and 562 can be electrically connected to the IMD 510 such as via separate conductors in the lead 508C such as to allow for sensing of the LV electrogram and optionally allow delivery of one or more resynchronization pacing pulses from the LV.

The IMD 510 can include an electronic circuit that can sense a physiologic signal. The physiologic signal can include an electrogram or a signal representing mechanical function of the heart 505. The hermetically sealed can 512 may function as an electrode such as for sensing or pulse delivery. For example, an electrode from one or more of the leads 508A-C may be used together with the can 512 such as for unipolar sensing of an electrogram or for delivering one or more pacing pulses. A defibrillation electrode from the lead 508B may be used together with the can 512 such as for delivering one or more cardioversion/defibrillation pulses. In an example, the IMD 510 can sense impedance such as between electrodes located on one or more of the leads 508A-C or the can 512. The IMD 510 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 510 can be configured to inject current between an electrode on the RV lead 508B and the can 512, and to sense the resultant voltage between the same electrodes or between a different electrode on the RV lead 508B and the can 512. A physiologic signal can be sensed from one or more physiologic sensors that can be integrated within the IMD 510. The IMD 510 can also be configured to sense a physiologic signal from one or more external physiologic sensors or one or more external electrodes that can be coupled to the IMD 510. Examples of the physiologic signal can include one or more of heart rate, heart rate variability, intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are.

The CRM system 500 can include a patient chronic condition-based HF assessment circuit, such as illustrated in the commonly assigned Qi An et al., U.S. application Ser. No. 14/55,392, incorporated herein by reference in its entirety. The patient chronic condition-based HF assessment circuit can include a signal analyzer circuit and a risk stratification circuit. The signal analyzer circuit can receive patient chronic condition indicators and one or more physiologic signals from the patient, and select one or more patient-specific sensor signals or signal metrics from the physiologic signals. The signal analyzer circuit can receive the physiologic signals from the patient using the electrodes on one or more of the leads 508A-C, or physiologic sensors deployed on or within the patient and communicated with the IMD 510. The risk stratification circuit can generate a composite risk index indicative of the probability of the patient later developing an event of worsening of HF (e.g., an HF decompensation event) such as using the selected patient-specific sensor signals or signal metrics. The HF decompensation event can include one or more early precursors of an HF decompensation episode, or an event indicative of HF progression such as recovery or worsening of HF status.

The external system 520 can allow for programming of the IMD 510 and can receives information about one or more signals acquired by IMD 510, such as can be received via a communication link 503. The external system 520 can include a local external IMD programmer. The external system 520 can include a remote patient management system that can monitor patient status or adjust one or more therapies such as from a remote location.

The communication link 503 can include one or more of an inductive telemetry link, a radio-frequency telemetry link, or a telecommunication link, such as an internet connection. The communication link 503 can provide for data transmission between the IMD 510 and the external system 520. The transmitted data can include, for example, real-time physiologic data acquired by the IMD 510, physiologic data acquired by and stored in the IMD 510, therapy history data or data indicating IMD operational status stored in the IMD 510, one or more programming instructions to the IMD 510 such as to configure the IMD 510 to perform one or more actions that can include physiologic data acquisition such as using programmably specifiable sensing electrodes and configuration, device self-diagnostic test, or delivery of one or more therapies.

The patient chronic condition-based HF assessment circuit, or other assessment circuit, may be implemented at the external system 520, which can be configured to perform HF risk stratification such as using data extracted from the IMD 510 or data stored in a memory within the external system 520. Portions of patient chronic condition-based HF or other assessment circuit may be distributed between the IMD 510 and the external system 520.

Portions of the IMD 510 or the external system 520 can be implemented using hardware, software, or any combination of hardware and software. Portions of the IMD 510 or the external system 520 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 510, the CRM system 500 could include a subcutaneous medical device (e.g., subcutaneous ICD, subcutaneous diagnostic device), wearable medical devices (e.g., patch based sensing device), or other external medical devices.

Figure 6:
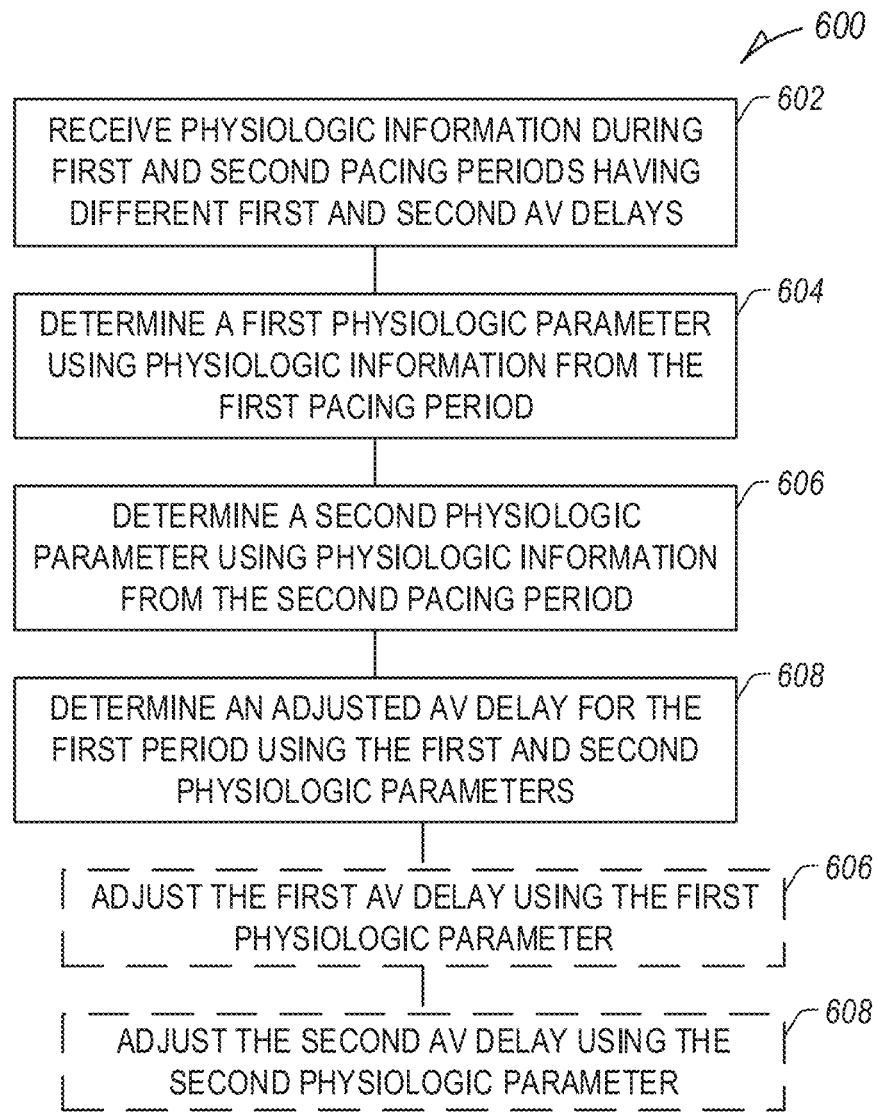
FIG. 6 illustrates an example method to determine an adjusted atrioventricular (AV) delay using determined first and second physiologic parameters.

FIG. 6 illustrates an example method 600 to determine an adjusted atrioventricular (AV) delay using determined first and second physiologic parameters. At 602, physiologic information is received from a patient, such as using a signal receiver circuit, or using one or more sensors, such as one or more sensors in, on, or associated with an ambulatory medical device (AMD), during a first pacing period in response to pacing a heart of the patient at a first atrioventricular (AV) delay, and separately or distinctly, during a second pacing period in response to pacing the heart of the patient at a second AV delay, different from the first AV delay.

At 604, a first physiologic parameter is determined using physiologic information received or sensed during the first pacing period. At 606, a second physiologic parameter is determined using physiologic information received or sensed during the second pacing period.

At 608, an adjusted AV delay can be determined for the first period using the first and second physiologic parameters. At 612, the first AV delay can be adjusted using the first physiologic parameter. At 614, the second AV delay can be adjusted using the second physiologic parameter. In certain examples, one or both of the first and second parameters can be used to adjust one or both of the first or second AV delay values. In certain examples, an adjusted AV delay can be determined, but not adjusted. If the determined AV delay varies from an existing AV delay (e.g., by an absolute or relative threshold amount), a user can be alerted, or the determined AV delay value can be provided to the user.

Figure 7:
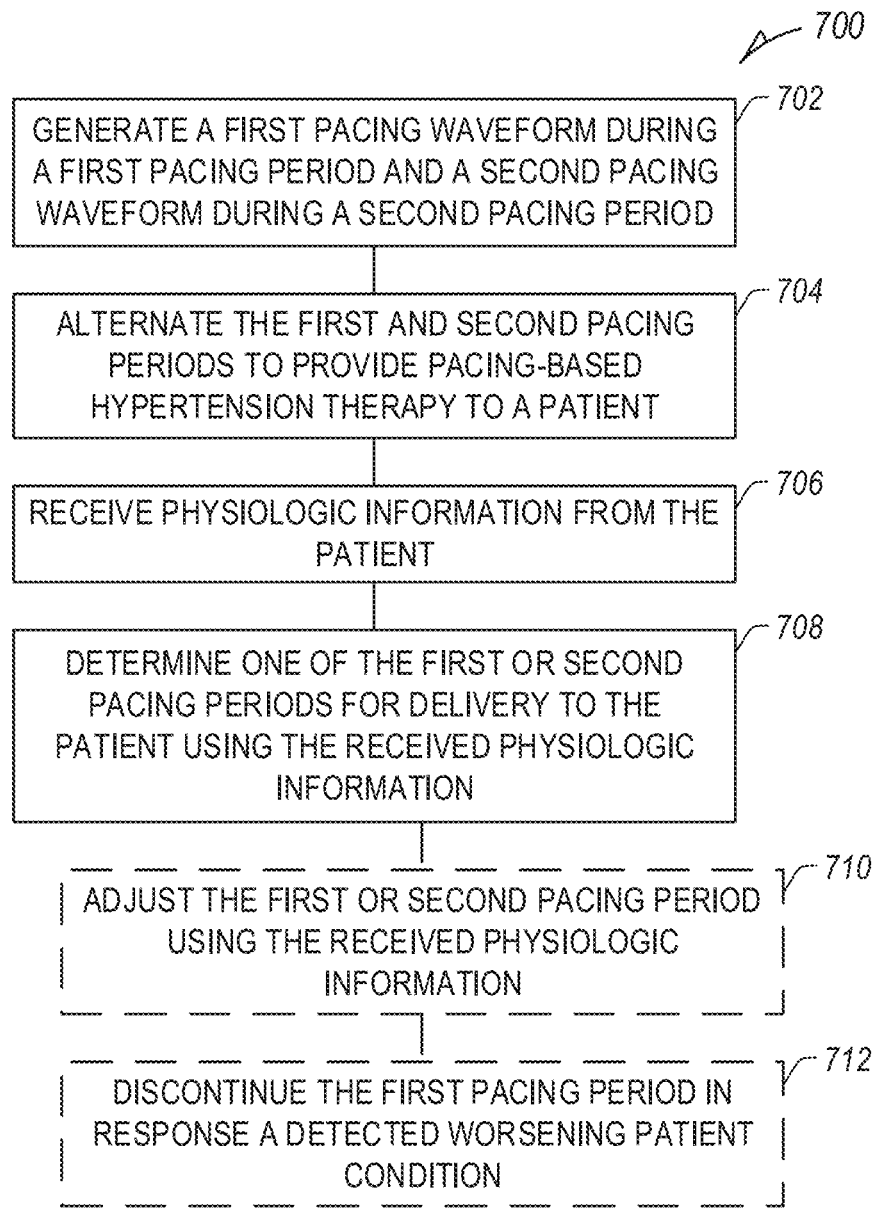
FIG. 7 illustrates an example method to determine a pacing period using received physiologic information.

FIG. 7 illustrates an example method 700 to determine a pacing period using received physiologic information. At 702, a first pacing waveform can be generated (e.g., using a stimulation circuit) during a first pacing period and a second pacing waveform can be generated during a second pacing period. At 704, the first and second pacing periods can be alternated to provide pacing-based hypertension therapy to a heart of a patient to reduce patient blood pressure. The first pacing waveform can have a first atrioventricular (AV) delay and the second pacing waveform can have a second AV delay longer than the first AV delay.

At 706, physiologic information can be received from the patient, such as using a signal receiver circuit. At 708, one of the first or second pacing periods are determined for delivery to the patient using the received physiologic information.

At 710, the first or second pacing period can be adjusted using the received physiologic information. At 712, the first pacing period can be discontinued or changed in response to a detected worsening patient condition.

Figure 8:
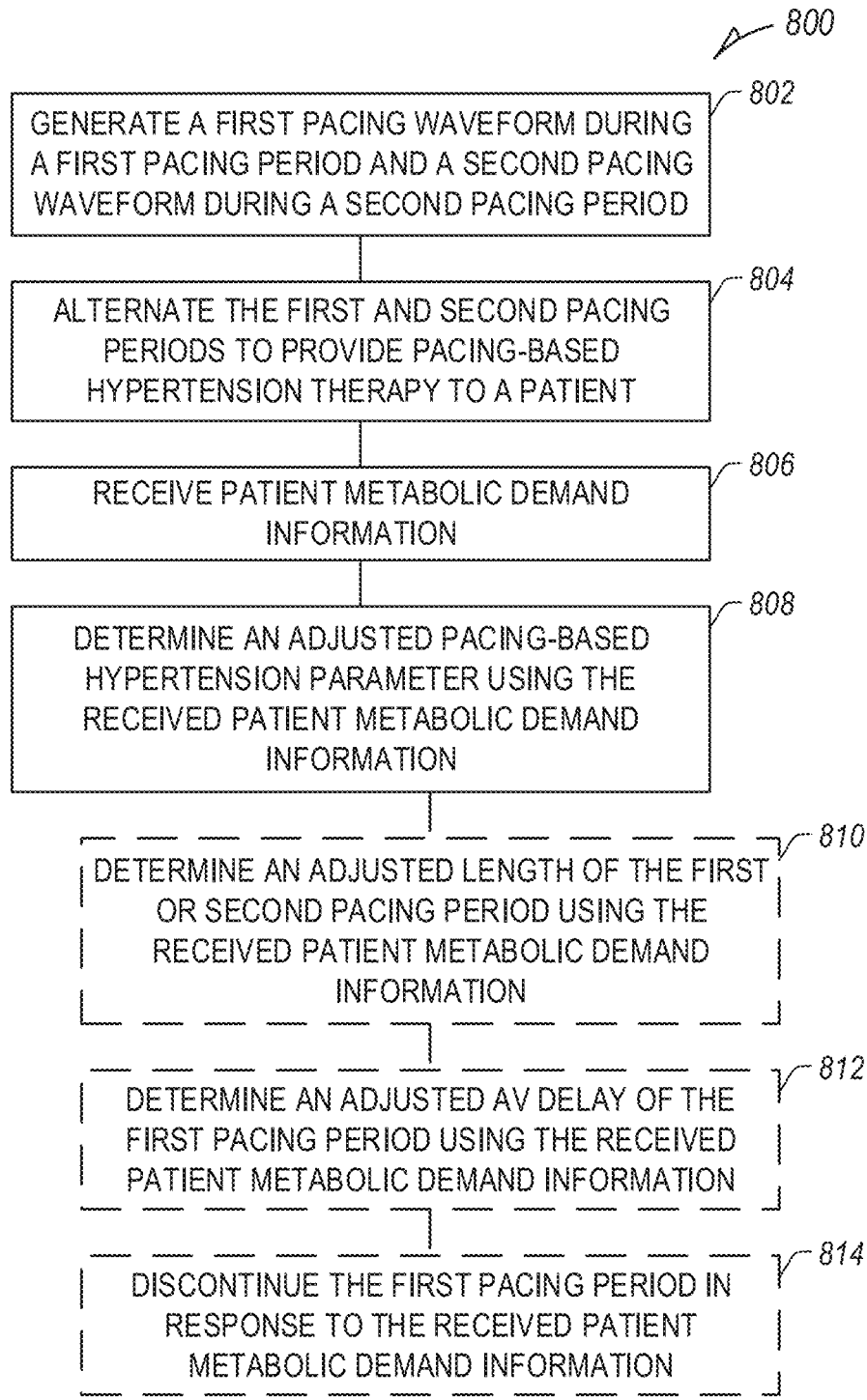
FIG. 8 illustrates an example method to determine an adjusted pacing-based hypertension parameter using received patient metabolic demand information.

FIG. 8 illustrates an example method 800 to determine an adjusted pacing-based hypertension parameter using received patient metabolic demand information. At 802, a first pacing waveform can be generated (e.g., using a stimulation circuit) during a first pacing period and a second pacing waveform can be generated during a second pacing period. At 804, the first and second pacing periods can be alternated to provide pacing-based hypertension therapy to a heart of a patient to reduce patient blood pressure. The first pacing waveform can have a first atrioventricular (AV) delay and the second pacing waveform can have a second AV delay longer than the first AV delay.

At 806, information can be received indicative of patient metabolic demand (e.g., activity information, respiration information, posture information, etc.). At 808, an adjusted pacing-based hypertension parameter can be determined using the received information indicative of patient metabolic demand.

At 810, an adjusted length (e.g., number of beats, etc.) of the first or second pacing period can be determined using the received information indicative of patient metabolic demand. At 812, an adjusted AV delay (e.g., AV delay value) of the first pacing period can be determined using the received information indicative of patient metabolic demand. At 814, the first pacing period (e.g., having the shorter AV delay) can be discontinued in response to the received information indicative of patient metabolic demand. For example, if periods of activity are detected, the pacing-based hypertension therapy can be discontinued.

Figure 9:
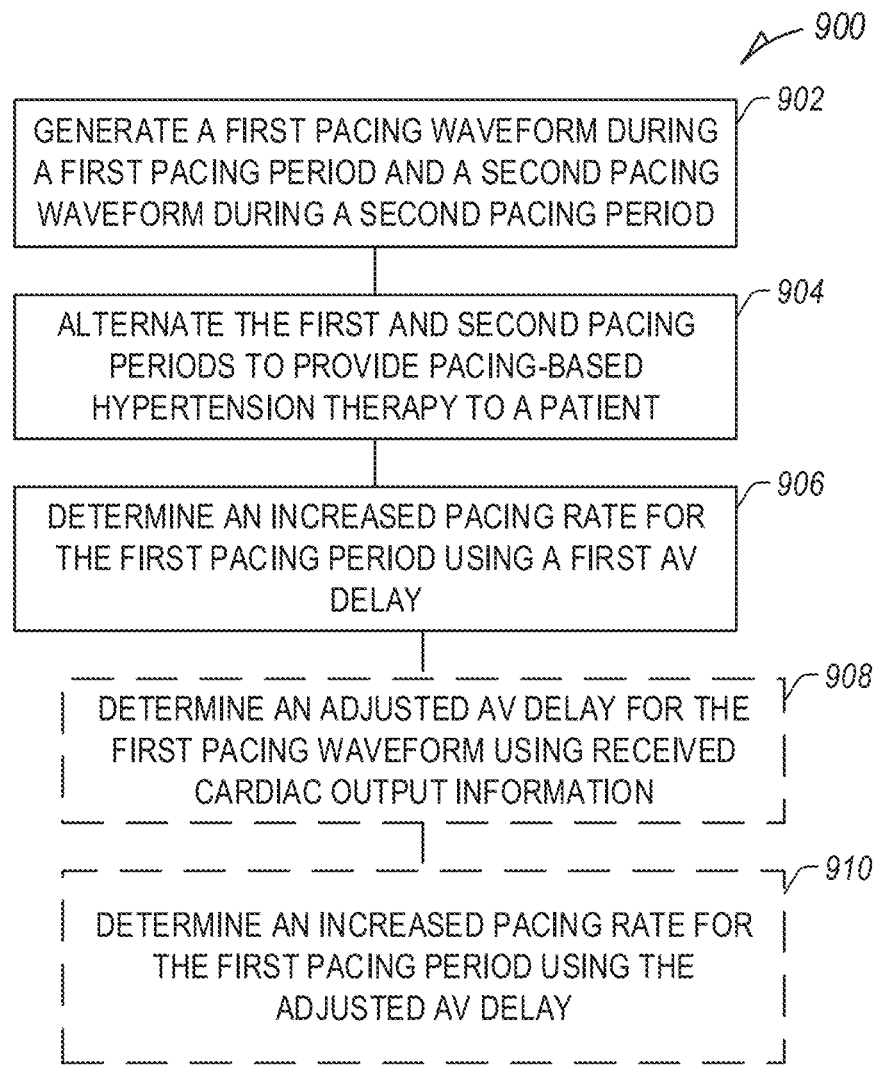
FIG. 9 illustrates an example method to determine an increased pacing rate for a pacing period using a first AV delay.

FIG. 9 illustrates an example method 900 to determine an increased pacing rate for a pacing period using a first AV delay. At 902, a first pacing waveform can be generated (e.g., using a stimulation circuit) during a first pacing period and a second pacing waveform can be generated during a second pacing period. At 904, the first and second pacing periods can be alternated to provide pacing-based hypertension therapy to a heart of a patient to reduce patient blood pressure. The first pacing waveform can have a first atrioventricular (AV) delay and the second pacing waveform can have a second AV delay longer than the first AV delay.

At 906, an increased pacing rate for the first pacing period can be determined using the first AV delay. If the first AV delay is adjusted, increased, or decreased, the pacing rate for the first pacing period can be adjusted accordingly to increase cardiac output during the periods of shorter AV delay values.

At 908, an adjusted AV delay for the first pacing waveform can be determined using received cardiac output information. At 910, an increased pacing rate for the first pacing period can be determined using the adjusted AV delay.

In any one or more of the preceding examples, parameters can be determined, but not implemented. In certain examples, determined parameters can be provided to a user, such as a clinician, to determine whether or not to implement. In other examples, determined parameters can be implemented once determined (e.g., if such changes fall within established save zones, etc.). Further, such changes and determinations provide improvement to existing therapy devices, in certain examples, including the stimulation circuits, signal receiver circuits, or assessments circuits disclosed herein. Implementing therapy adjustments, or providing determined adjustments to a user for consideration, can speed therapy or recovery time of a patient, such as by providing optimized (or more optimized) therapy, or by reducing periods of less effective or ineffective therapy, extending the usable life of existing AMDs.

Figure 10:
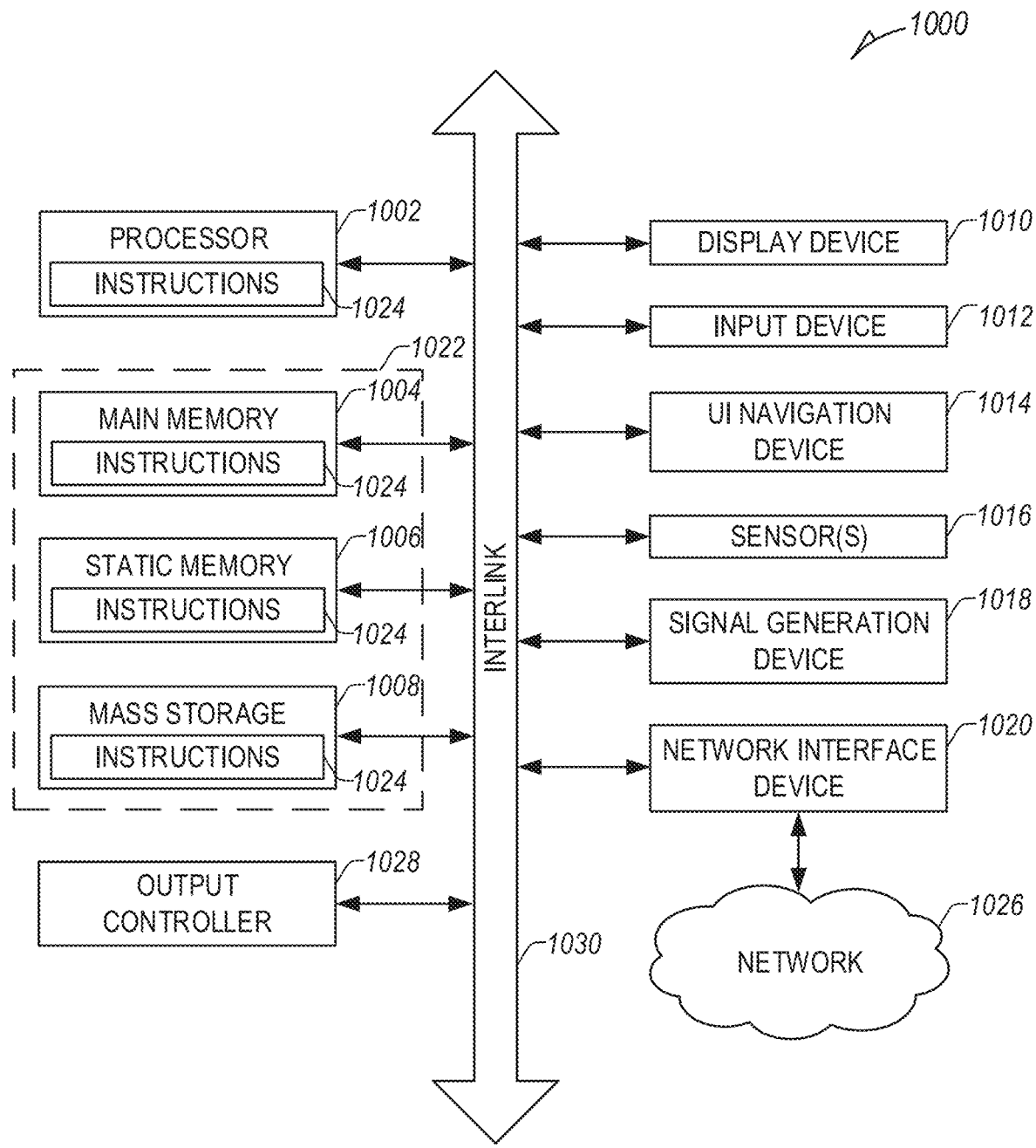
FIG. 10 illustrates a block diagram of an example machine upon which any one or more of the techniques (e.g., methodologies) discussed herein may perform.

FIG. 10 illustrates a block diagram of an example machine 1000 upon which any one or more of the techniques (e.g., methodologies) discussed herein may perform. Portions of this description may apply to the computing framework of one or more of the medical devices described herein, such as the IMD, the external programmer, etc.

Examples, as described herein, may include, or may operate by, logic or a number of components, or mechanisms in the machine 1000. Circuitry (e.g., processing circuitry) is a collection of circuits implemented in tangible entities of the machine 1000 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 1000 follow.

In alternative embodiments, the machine 1000 may operate as a standalone device or may be connected (e.g., networked) to other machines. In a networked deployment, the machine 1000 may operate in the capacity of a server machine, a client machine, or both in server-client network environments. In an example, the machine 1000 may act as a peer machine in peer-to-peer (P2P) (or other distributed) network environment. The machine 1000 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 1000 may include a hardware processor 1002 (e.g., a central processing unit (CPU), a graphics processing unit (GPU), a hardware processor core, or any combination thereof), a main memory 1004, a static memory (e.g., memory or storage for firmware, microcode, a basic-input-output (BIOS), unified extensible firmware interface (UEFI), etc.) 1006, and mass storage 1008 (e.g., hard drive, tape drive, flash storage, or other block devices) some or all of which may communicate with each other via an interlink (e.g., bus) 1030. The machine 1000 may further include a display unit 1010, an alphanumeric input device 1012 (e.g., a keyboard), and a user interface (UI) navigation device 1014 (e.g., a mouse). In an example, the display unit 1010, input device 1012, and UI navigation device 1014 may be a touch screen display. The machine 1000 may additionally include a signal generation device 1018 (e.g., a speaker), a network interface device 1020, and one or more sensors 1016, such as a global positioning system (GPS) sensor, compass, accelerometer, or one or more other sensors. The machine 1000 may include an output controller 1028, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 1002, the main memory 1004, the static memory 1006, or the mass storage 1008 may be, or include, a machine-readable medium 1022 on which is stored one or more sets of data structures or instructions 1024 (e.g., software) embodying or utilized by any one or more of the techniques or functions described herein. The instructions 1024 may also reside, completely or at least partially, within any of registers of the processor 1002, the main memory 1004, the static memory 1006, or the mass storage 1008 during execution thereof by the machine 1000. In an example, one or any combination of the hardware processor 1002, the main memory 1004, the static memory 1006, or the mass storage 1008 may constitute the machine-readable medium 1022. While the machine-readable medium 1022 is illustrated as a single medium, the term "machine-readable medium" may include a single medium or multiple media (e.g., a centralized or distributed database, and/or associated caches and servers) configured to store the one or more instructions 1024.

The term "machine-readable medium" may include any medium that is capable of storing, encoding, or carrying instructions for execution by the machine 1000 and that cause the machine 1000 to perform any one or more of the techniques of the present disclosure, or that is capable of storing, encoding or carrying data structures used by or associated with such instructions. Non-limiting machine-readable medium examples may include solid-state memories, optical media, magnetic media, and signals (e.g., radio frequency signals, other photon based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1024 may be further transmitted or received over a communications network 1026 using a transmission medium via the network interface device 1020 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1020 may include one or more physical jacks (e.g., Ethernet, coaxial, or phone jacks) or one or more antennas to connect to the communications network 1026. In an example, the network interface device 1020 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1000, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system comprising:
   a stimulation circuit configured to generate a first pacing waveform first and second pacing waveforms;
   a signal receiver circuit configured to receive physiologic information from the patient, and
   an assessment circuit configured to control generation of the first and second pacing waveforms to provide patterned-pacing-based hypertension therapy to a heart of a patient, including to control generation of the first pacing waveform having a first atrioventricular (AV) delay during a first pacing period to reduce patient blood pressure and the second pacing waveform having a second AV delay, longer than the first AV delay, to prevent an increase in patient blood pressure during a second pacing period, and to dynamically alternate the first and second pacing periods, based on the received physiologic information, to provide a dynamic pattern of first and second pacing waveforms to reduce patient blood pressure.

2. The system of claim 1, wherein the assessment circuit is configured to adjust the first or second pacing period using the received physiologic information.

3. The system of claim 1, wherein the assessment circuit is configured to detect a patient condition using the received physiologic information, and wherein to dynamically alternate the first and second pacing periods includes to reduce the first pacing period with respect to the second pacing period in response to a detected worsening patient condition.

4. The system of claim 3, wherein the assessment circuit is configured to detect an arrhythmia of the patient using the received physiologic information, and wherein to dynamically alternate the first and second pacing periods includes to reduce the first pacing period with respect to the second pacing period in response to a number of detected arrhythmias over a threshold time period.

5. The system of claim 1, wherein the assessment circuit is configured to determine an arrhythmia metric of the patient using the received physiologic information, and to dynamically alternate the first and second pacing periods using the determined arrhythmia metric.

6. The system of claim 1, wherein the assessment circuit is configured to determine a heart failure metric of the patient using the received physiologic information, and to dynamically alternate the first and second pacing periods using the determined heart failure metric.

7. The system of claim 1, wherein the signal receiver circuit is configured to receive third heart sound (S3) information and fourth heart sound (S4) information from the patient, and
   wherein the assessment circuit is configured to determine an indication of early-to-late ventricular-filling velocities (E/A ratio) using the S3 information and the S4 information, and to dynamically alternate the first and second pacing periods using the determined E/A ratio.

8. The system of claim 1, wherein the signal receiver circuit is configured to receive first heart sound (S1) information from the patient, and
   wherein the assessment circuit is configured to determine an indication of long-term impact of the first pacing period to the patient using S1 information detected during the second pacing period, and to dynamically alternate the first and second pacing periods using the determined indication of long-term impact.

9. The system of claim 1, wherein the signal receiver circuit is configured to receive first heart sound (S1) information and second heart sound (S2) information from the patient, and
   wherein the assessment circuit is configured to determine an S1 metric and an S2 metric for the patient over the first and second pacing periods, and to adjust the first or second pacing periods to reduce the S2 metric without reducing the S1 metric.

10. The system of claim 1, wherein the assessment circuit is configured to, in response to the determined first or second pacing period, provide an indication to a user to adjust the pacing-based hypertension therapy to the patient.

11. At least one non-transitory machine-readable medium including instructions that, when performed by a medical device, cause the medical device to:
    generate a first pacing waveform during a first pacing period and a second pacing waveform during a second pacing period to provide pacing-based hypertension therapy to a heart of a patient to reduce patient blood pressure, wherein the first pacing waveform has a first atrioventricular (AV) delay to reduce patient blood pressure and the second pacing waveform has a second AV delay longer than the first AV delay to prevent an increase in patient blood pressure during the second pacing period;
    receive physiologic information from the patient; and
    dynamically alternate the first and second pacing periods, based on the received physiologic information, to provide a dynamic pattern of first and second pacing waveforms to reduce patient blood pressure.

12. The at least one machine-readable medium of claim 11, wherein the instructions, when performed by the medical device, cause the medical device to:
    adjust the first or second pacing period using the received physiologic information.

13. The at least one machine-readable medium of claim 11, wherein the instructions, when performed by the medical device, cause the medical device to:
    detect a patient condition using the received physiologic information, wherein to dynamically alternate the first and second pacing periods includes to reduce the first pacing period with respect to the second pacing period in response to a detected worsening patient condition.

14. The at least one machine-readable medium of claim 11, wherein the instructions, when performed by the medical device, cause the medical device to:

detect an arrhythmia of the patient using the received physiologic information, wherein to dynamically alternate the first and second pacing periods includes to reduce the first pacing period with respect to the second pacing period in response to a number of detected arrhythmias over a threshold time period.

15. The at least one machine-readable medium of claim 11, wherein the instructions, when performed by the medical device, cause the medical device to:

determine an arrhythmia metric of the patient using the received physiologic information, and to adjust the first or second pacing period using the determined arrhythmia metric.

16. A method comprising:

generating, using a stimulation circuit, a first pacing waveform during a first pacing period and a second pacing waveform during a second pacing period to provide pacing-based hypertension therapy to a heart of a patient to reduce patient blood pressure, wherein the first pacing waveform has a first atrioventricular (AV) delay to reduce patient blood pressure and the second pacing waveform has a second AV delay longer than the first AV delay to prevent an increase in patient blood pressure during the second pacing period;

receiving, using a signal receiver circuit, physiologic information from the patient; and dynamically alternating the first and second pacing periods, based on the received physiologic information, to provide a dynamic pattern of first and second pacing waveforms to reduce patient blood pressure.

17. The method of claim 16, including:

adjusting, using the assessment circuit, the first or second pacing period using the received physiologic information.

18. The method of claim 16, including:

detecting, using the assessment circuit, a patient condition using the received physiologic information, dynamically alternating the first and second pacing periods includes reducing the first pacing period with respect to the second pacing period in response to a detected worsening patient condition.

19. The method of claim 18, including:

detecting, using the assessment circuit, an arrhythmia of the patient using the received physiologic information, wherein dynamically alternating the first and second pacing periods includes reducing the first pacing period with respect to the second pacing period in response to a number of detected arrhythmias over a threshold time period.

20. The method of claim 16, including:

determining, using the assessment circuit, an arrhythmia metric of the patient using the received physiologic information; and adjusting, using the assessment circuit, the first or second pacing period using the determined arrhythmia metric.

* * * * *